US008378000B2

(12) United States Patent
Hintz et al.

(10) Patent No.: US 8,378,000 B2
(45) Date of Patent: Feb. 19, 2013

(54) WATER-ABSORBENT, FOAM-TYPE POLYMER STRUCTURE

(75) Inventors: Sandra Hintz, Moers (DE); Helmut Bruggemann, Moers (DE)

(73) Assignee: Evonik Stockhausen GmbH, Krefeld (DE)

(*) Notice: Subject to any disclaimer, the term of this patent is extended or adjusted under 35 U.S.C. 154(b) by 927 days.

(21) Appl. No.: 10/520,697

(22) PCT Filed: Jul. 9, 2003

(86) PCT No.: PCT/EP03/07425
§ 371 (c)(1),
(2), (4) Date: Apr. 5, 2005

(87) PCT Pub. No.: WO2004/006971
PCT Pub. Date: Jan. 22, 2004

(65) Prior Publication Data
US 2005/0176834 A1 Aug. 11, 2005

(30) Foreign Application Priority Data
Jul. 11, 2002 (DE) .................................. 102 31 356

(51) Int. Cl.
*C08J 9/00* (2006.01)
*C08J 9/04* (2006.01)
(52) U.S. Cl. .......................................... 521/50; 521/908
(58) Field of Classification Search .................... 521/50, 521/908
See application file for complete search history.

(56) References Cited

U.S. PATENT DOCUMENTS

| RE26,151 | E | 1/1967 | Duncan et al. | |
|---|---|---|---|---|
| 3,489,148 | A | 1/1970 | Duncan et al. | |
| 3,592,194 | A | 7/1971 | Duncan et al. | |
| 3,812,225 | A * | 5/1974 | Hosoda et al. | 264/54 |
| 3,860,003 | A | 1/1975 | Buell | |
| 4,394,930 | A * | 7/1983 | Korpman | 220/62.18 |
| 4,883,478 | A | 11/1989 | Lerailler et al. | |
| 5,061,295 | A | 10/1991 | Hickory et al. | |
| 5,118,719 | A | 6/1992 | Lind | |
| 5,149,335 | A | 9/1992 | Kellenberger et al. | |
| 5,154,713 | A | 10/1992 | Lind | |
| 5,260,345 | A | 11/1993 | DesMarais et al. | |
| 5,290,870 | A | 3/1994 | Ahmed et al. | |
| 5,672,633 | A | 9/1997 | Brehm et al. | |
| 5,712,316 | A | 1/1998 | Dahmen et al. | |
| 5,840,777 | A * | 11/1998 | Eagles et al. | 521/82 |
| 5,948,829 | A | 9/1999 | Wallajapet et al. | |
| 5,985,434 | A * | 11/1999 | Qin et al. | 428/315.5 |
| 6,001,911 | A * | 12/1999 | Ishizaki et al. | 524/388 |
| 6,033,769 | A * | 3/2000 | Brueggemann et al. | 428/305.5 |
| 6,136,873 | A | 10/2000 | Hahnle et al. | |
| 6,174,929 | B1 | 1/2001 | Hahnle et al. | |
| 6,455,600 | B1 | 9/2002 | Hahnle et al. | |
| 6,750,262 | B1 * | 6/2004 | Hahnle et al. | 521/64 |
| 2001/0024716 | A1 * | 9/2001 | Chen et al. | 428/317.9 |

FOREIGN PATENT DOCUMENTS

| DE | 19540951 A1 | 5/1997 |
|---|---|---|
| DE | 19607551 A1 | 9/1997 |
| DE | 19809540 A1 | 9/1999 |
| DE | 19909214 A1 | 9/2000 |
| EP | 0 293 762 | 12/1988 |
| EP | 0 347 241 | 12/1989 |
| EP | 0 427 219 A2 | 5/1991 |
| EP | 0744435 A1 | 11/1996 |
| EP | 0707603 B1 | 9/1997 |
| EP | 0802238 A1 | 10/1997 |
| JP | 5-237378 | 9/1993 |
| JP | 2002-020500 | 1/2002 |
| WO | 8703208 A1 | 6/1987 |
| WO | WO 88/09801 | 12/1988 |
| WO | WO 94/22502 | 10/1994 |
| WO | 9502002 A1 | 1/1995 |
| WO | WO 95/32860 | 12/1995 |
| WO | WO 96/21181 | 7/1996 |
| WO | WO 96/21680 | 7/1996 |
| WO | WO 96/25958 | 8/1996 |
| WO | WO 96/31555 | 10/1996 |
| WO | WO 97/17397 | 5/1997 |
| WO | WO 98/00181 | 1/1998 |
| WO | 0052087 A1 | 9/2000 |
| WO | WO 00/52087 * | 9/2000 |
| WO | 03026707 A2 | 4/2003 |

OTHER PUBLICATIONS

International Search Report mailed on Jan. 23, 2004 in connection with PCT/EP03/07425.
F.L. Buchholz and A.T. Graham, "Modern Superabsorbent Polymer Technology," Copyright 1998, pp. 199-215, John Wiley & Sons, Inc.

* cited by examiner

*Primary Examiner* — Peter F Godenschwager
(74) *Attorney, Agent, or Firm* — Smith Moore Leatherwood LLP; Philip P. McCann

(57) ABSTRACT

The present invention relates to a process for the preparation of water-absorbent, foam-type polymer structures, wherein an aqueous composition is foamed, and the foamed aqueous composition is then heated at a temperature in a range of from 50 to 300° C., so that the polymer crosslinks at least partially and the content of water is adjusted to not more than 15 wt. %, based on the total weight of the foam-type polymer structure that forms.

15 Claims, No Drawings

WATER-ABSORBENT, FOAM-TYPE POLYMER STRUCTURE

This application is a national stage application under 35 U.S.C. 371 of international application no. PCT/EP2003/007425 filed Jul. 9, 2003, which is based on German Application no. DE 102.31 356.3, filed on Jul. 11, 2002, and claims priority thereto.

BACKGROUND TO THE PRESENT INVENTION

The present invention relates to a process for the preparation of a water-absorbent, foam-type polymer structure, to a water-absorbent, foam-type polymer structure obtainable by that process, to a water-absorbent, foam-type polymer structure, to a composite comprising a water-absorbent, foam-type polymer structure and a substrate, to a process for the production of the composite, to composites obtainable by that process, to the use of the water-absorbent, foam-type polymer structure, and to chemical products.

Water-absorbent polymers are referred to as superabsorbers or superabsorbent polymers, because they are capable of absorbing a multiple of their own weight in aqueous liquids with the formation of hydrogels. In practice, such superabsorbers are used, for example, in diapers to absorb urine. They have the property of retaining the absorbed liquid even under mechanical load.

Superabsorbers are nowadays used predominantly in powder form. Within the scope of simplifications to processes, it is desirable to use superabsorbers in a fixed form, for example to incorporate them into a foamed matrix. According to the prior art there are two different types of foamed systems.

The first type is a foamed matrix that contains prefabricated superabsorber granules. For example, EP-A-0 427 219 describes mixtures of superabsorbent polymers and latex foams. The foamed matrix in this case serves to fix the superabsorber granules and to distribute the liquid. However, the matrix itself makes only a very limited contribution to the absorption of the liquid.

The second type are foams which themselves consist of superabsorbent material. Three different processes are described in the literature for producing such foams. They can be produced (i) by polymerization of a monomer solution in a water-in-oil polymer dispersion, (ii) by foaming of a monomer solution and subsequent polymerization or (iii) by thermal foaming of a polymer with the addition of blowing or expanding agents.

WO 96/21680 and WO 96/21181, for example, describe a foam produced by a process of type (i). In that process, a monomer mixture that contains an emulsified aqueous phase is polymerized. The water serves to keep space available for the pores of the foam, which form later. However, the foams described in that document exhibit poor retention.

WO 94/22502 describes a foam, which is obtained by a process of type (ii) and is based on partially neutralised polyacrylates. The foam is produced by foaming a monomer mixture using a water-soluble expanding agent, such as Freon 1,1,2. The disadvantage of the foams described in that document is their poor rate of absorption.

In WO 97/17397 absorbent foams are obtained by foaming a monomer solution using blowing agents according to a process of type (ii). The disadvantage of the foams described in that document is their hardness and brittleness. It is necessary to incorporate plasticizers into the foams in order to process them.

U.S. Pat. No. 4,394,930 describes absorbent polymer foams produced by a process of type (iii). In the process described in that document, prefabricated superabsorbers, such as, for example, starch copolymers, are foamed thermally on a substrate, such as, for example, a cellulose nonwoven or a polyethylene film, with the addition of blowing agents. The foams obtained by that process are hard and have little flexibility.

WO 88/0981 also describes absorbent polymer foams obtained by a process of type (iii). A terpolymer of ethyl acrylate, Na acrylate and Na methacrylate is foamed thermally in the presence of expanding agents, such as, for example, sodium hydrogen carbonate. However, because of the low polyelectrolyte content, the foams described in that document have poor retention.

The object according to the present invention is, generally, to overcome the disadvantages arising from the prior art.

A further object underlying this present invention is to provide absorbent polymer foams, which exhibit satisfactory properties, both in respect of retention and in respect of the rate of absorption and absorption under load.

A further object according to the present invention is to provide absorbent foams, which possess a high degree of softness and flexibility, even though they consist of a homogeneous polymer, and which do not require the incorporation of prefabricated superabsorber granules.

A further object underlying this present invention is to provide a process with which such foams can be produced using starting compounds that are as inexpensive as possible and, where possible, without using halogenated hydrocarbons as expanding agents.

Finally, an object according to the present invention consists in providing composites, especially hygiene articles and components thereof, which, in addition to the absorption properties, are very comfortable to wear and, in particular, do not restrict the movements of the user.

BRIEF SUMMARY OF THE PRESENT INVENTION

The above objects are achieved by a process for the production of water-absorbent, foam-type polymer structures, wherein an aqueous composition (A) containing
(A1) water,
(A2) one or more polymers based at least on
($\alpha$1) from about 55 to 100 wt. %, preferably from about 55 to about 99.9 wt. % and particularly preferably from about 70 to about 90 wt. %, of a polymerized, monoethylenically unsaturated, acid-group-containing monomer or its salt, and on
($\alpha$2) from 0 to about 45 wt. %, preferably from about 0.1 to about 45 wt. % and particularly preferably from about 10 to about 30 wt. %, of a polymerized, monoethylenically unsaturated monomer that is copolymerizable with ($\alpha$1),
wherein the sum of the amounts by weight of ($\alpha$1) and ($\alpha$2) is 100 wt. % and wherein at least about 31.5 wt. % of the monomers, preferably at least about 50 wt. % and particularly preferably at least about 75 wt. %, in each case based on the total weight of the monomers ($\alpha$1) and ($\alpha$2), are acrylic acid or salts of acrylic acid,
(A3) one or more crosslinkers,
(A4) one or more blowing agents,
(A5) one or more surfactants,
(A6) and optionally further auxiliary substances,
is foamed, and the foamed aqueous composition is then heated at a temperature in a range of from about 50 to about 300° C., preferably in a range of from about 100 to about 250° C., so that, preferably whereby, the polymer (A2) crosslinks at least partially and the content of water (A1) is adjusted to not more than about 15 wt. %, preferably to not more than 10 wt. % and particularly preferably to not more than about 5 wt. %, in each case based on the total weight of the foam-type polymer structure that forms and in each case determined by the oven method according to ERT 430.1-99.

In another embodiment of the process according to the present invention, the foam-type polymer structure obtained above can be brought into contact at least once more with at least one crosslinker. Preferred crosslinkers are the crosslinkers (A3). The further crosslinking of the foam-type polymer structure is preferably carried out thermally, preferably in a range of from about 50 to about 300° C. and particularly preferably in a range of from about 120 to about 200° C. The crosslinking particularly preferably takes place more intensely in the region of the surface of the foam-type polymer structure.

In a preferred embodiment of the process according to the present invention, at least about 50-mol %, preferably at least about 90-mol % and particularly preferably at least about 99.9 mol % of the monomers of the polymer (A2) are soluble in water.

DETAILED DESCRIPTION OF THE INVENTION

The monoethylenically unsaturated, acid-group-containing monomers ($\alpha$1) may be partially or completely, preferably partially, neutralised. The monoethylenically unsaturated, acid-group-containing monomers are preferably neutralised to the extent of at least about 25 mol %, particularly preferably to the extent of at least about 50 mol % and more preferably to the extent of from about 50 to about 90 mol %. Neutralization of the monomers ($\alpha$1) can be carried out before or after the polymerization. The neutralization can be carried out using alkali metal hydroxides, alkaline earth metal hydroxides, ammonia as well as carbonates and bicarbonates. In addition, any further base that forms a water-soluble salt with the acid is possible. Mixed neutralization using different bases is also possible. Preference is given to neutralization using ammonia or alkali metal hydroxides, particularly preferably using sodium hydroxide or ammonia.

Preferred monoethylenically unsaturated, acid-group-containing monomers ($\alpha$1) are acrylic acid, methacrylic acid, ethacrylic acid, $\alpha$-chloroacrylic acid, $\alpha$-cyanoacrylic acid, $\beta$-methylacrylic acid (crotonic acid), $\alpha$-phenylacrylic acid, $\beta$-acryloxypropionic acid, sorbic acid, $\alpha$-chlorosorbic acid, 2'-methylisocrotonic acid, cinnamic acid, p-chlorocinnamic acid, $\beta$-stearyl acid, itaconic acid, citraconic acid, mesaconic acid, glutaconic acid, aconitic acid, maleic acid, fumaric acid, tricarboxyethylene and maleic anhydride, with acrylic acid and methacrylic acid being particularly preferred and acrylic acid being more preferred.

In addition to those carboxylate-group-containing monomers, ethylenically unsaturated sulfonic acid monomers or ethylenically unsaturated phosphonic acid monomers are also preferred as monoethylenically unsaturated, acid-group-containing monomers ($\alpha$1).

Preferred ethylenically unsaturated sulfonic acid monomers are allylsulfonic acid or aliphatic or aromatic vinylsulfonic acids or acrylic or methacrylic sulfonic acids. Preferred aliphatic or aromatic vinylsulfonic acids are vinylsulfonic acid, 4-vinyl-benzylsulfonic acid, vinyltoluenesulfonic acid and styrenesulfonic acid. Preferred acrylic- and methacrylic-sulfonic acids are sulfoethyl (meth)acrylate, sulfopropyl (meth)acrylate, 2-hydroxy-3-methacryloxypropylsulfonic acid and 2-acrylamido-2-methylpropanesulfonic acid.

Also preferred are ethylenically unsaturated phosphonic acid monomers, such as vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acrylic-phosphonic acid derivatives.

Preferred monoethylenically unsaturated monomers ($\alpha$2) that are copolymerizable with ($\alpha$1) are amides and nitriles of monoethylenically unsaturated carboxylic acids, such as, for example, acrylamide, methacrylamide and N-vinylformamide, acrylonitrile and methacrylonitrile, dialkyldiallylammonium halides, such as dimethyldiallylammonium chloride, diethyldiallylammonium chloride, allylpiperidinium bromide, N-vinylimidazoles, such as N-vinylimidazole, 1-vinyl-2-methylimidazole, and N-vinylimidazolines, such as N-vinylimidazoline, 1-vinyl-2-methylimidazoline, 1-vinyl-2-ethylimidazoline or 1-vinyl-2-propylimidazoline, which can be used in the polymerization in the form of the free bases, in quaternized form or in salt form. Also suitable are dialkylaminoalkyl acrylates and dialkylaminoalkyl methacrylates, for example dimethylaminoethyl acrylate, dimethylaminoethyl methacrylate, diethylaminoethyl acrylate and diethylaminoethyl methacrylate. Examples of other preferred monomers ($\alpha$2) include vinyl esters of saturated $C_1$-$C_4$-carboxylic acids, such as, for example, vinyl formate, vinyl acetate or vinyl propionate, alkyl vinyl ethers having at least two carbon atoms in the alkyl group, such as, for example, ethyl vinyl ether or butyl vinyl ether, esters of monoethylenically unsaturated $C_3$-$C_6$-carboxylic acids, such as, for example, esters of monohydric $C_1$-$C_8$-alcohols and acrylic acid, methacrylic acid or maleic acid, semi-esters of maleic acid, for example monomethyl maleate, and hydroxyalkyl esters of the mentioned monoethylenically unsaturated carboxylic acids, for example 2-hydroxyethyl acrylate, hydroxypropyl acrylate, hydroxybutyl acrylate, hydroxyethyl methacrylate, hydroxypropyl methacrylate and hydroxybutyl methacrylate, N-vinyllactams, such as, for example, N-vinylpyrrolidone or N-vinylcaprolactam, acrylic acid and methacrylic acid esters of alkoxylated, monohydric, saturated alcohols, for example of alcohols having from 10 to 25 carbon atoms, which have been reacted with from 2 to 200 mol of ethylene oxide and/or propylene oxide per mol of alcohol, as well as monoacrylic acid esters of polyethylene glycol or polypropylene glycol, wherein the molar masses of the polyalkylene glycols may be, for example, up to 2000. Suitable monomers ($\alpha$2) are also alkyl-substituted styrenes, such as ethylstyrene or tert.-butylstyrene.

The polymers (A2) can be prepared by various polymerization processes known per se. Preference is given to free-radical polymerization in homogeneous phase, especially in aqueous solution as so-called gel polymerization. Further possible methods are precipitation polymerization from organic solvents, such as, for example, from alcohols, or suspension, emulsion or microemulsion polymerization. In special cases, polymerizations that take place via an ionic mechanism may be used instead of free-radical polymerization. There may be used in the polymerization, in addition to the polymerization initiators, further adjuvants, such as, for example, chain regulators, such as mercaptoethanol.

As initiators for initiating the polymerization there may be used any initiators that form free radicals under the polymerization conditions and that are conventionally employed in the production of superabsorbers. It is also possible to initiate the polymerization by the action of electron beams on the polymerizable aqueous monomer mixture. The polymerization can also be initiated in the absence of initiators of the above-mentioned type by the action of high-energy radiation in the presence of photoinitiators.

Polymerization initiators are preferably peroxides, hydroperoxides, hydrogen peroxide, persulfates, azo compounds and the so-called redox catalysts. The use of water-soluble catalysts is preferred. In some cases it is advantageous to use mixtures of different polymerization initiators. Of such mixtures, preference is given to mixtures of hydrogen peroxide and sodium or potassium peroxodisulfate, which can be used in any conceivable relative proportions. Suitable organic peroxides are preferably acetyl acetone peroxide, methyl ethyl ketone peroxide, tert.-butyl hydroperoxide, cumene hydroperoxide, tert.-amyl perpivalate, tert.-butyl perpivalate, tert.-butyl perneohexonate, tert.-butyl isobutyrate, tert.-butyl per-2-ethylhexenoate, tert.-butyl perisononanoate, tert.-butyl permaleate, tert.-butyl perbenzoate, tert.-butyl 3,5,5-trimethylhexanoate and amyl perneodecanoate. The following are also preferred as polymerization initiators: azo compounds, such as 2,2'-azobis-(2-amidinopropane)dihydrochloride, azo-bis-amidinopropane dihydrochloride, 2,2'-azobis-(N,N-dimethylene)isobutyramidine dihydrochloride, 2-(carbamoylazo)isobutyronitrile and 4,4'-azobis-(4-cyanovaleric acid). The mentioned compounds are used in conventional amounts, preferably in a range of from 0.01 to 5-mol %, preferably from 0.1 to 2-mol %, in each case based on the amount of the monomers to be polymerized. The redox catalysts contain as the oxidic component at least one of the above-mentioned per compounds and as the reducing component preferably ascorbic acid, glucose, sorbose, mannose, ammonium or alkali metal hydrogen sulfite, sulfate, thiosulfate, hyposulfite or sulfide, metal salts, such as iron(II) ions or silver ions, or sodium hydroxymethyl sulfoxylate. Ascorbic acid or sodium pyrosulfite is preferably used as the reducing component of the redox catalyst. Based on the amount of monomers used in the polymerization, from about $1 \times 10^{-5}$ to about 1 mol % of the reducing component of the redox catalyst and from about $1 \times 10^{-5}$ to about 5 mol % of the oxidizing component of the redox catalyst are used. Instead of the oxidizing component of the redox catalyst, or in addition thereto, one or more azo compounds, preferably water-soluble azo compounds, can be used.

A redox system consisting of hydrogen peroxide, sodium peroxodisulfate and ascorbic acid is preferably used in the preparation of the polymers (A2). In general, azo compounds are preferred according to the present invention as initiators, with azo-bis-amidinopropane dihydrochloride being particularly preferred. In general, the polymerization is initiated using the initiators in a temperature range of from about 30 to about 90° C.

If the polymerization is initiated by the action of high-energy radiation, so-called photoinitiators are usually used as initiators. Photoinitiators may be, for example, so-called α-cleaving agents, H-radiating systems or azides. Examples of such initiators are benzophenone derivatives, such as Michlers ketone, phenanthrene derivatives, fluorene derivatives, anthraquinone derivatives, thioxanthone derivatives, coumarin derivatives, benzoin ethers and derivatives thereof, azo compounds, such as the free-radical generators mentioned above, substituted hexaarylbisimidazoles or acylphosphine oxides. Examples of azides are: (N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl-2-(N,N-dimethylamino)ethylsulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis (p-azidobenzylidene)-4-methylcyclohexanone.

In a preferred embodiment of the process according to the present invention, the polymers (A2) have a number-average molecular weight, determined by means of GPC, of at least about 10,000 g/mol, preferably of at least about 25,000 g/mol and more preferably of at least about 50,000 g/mol, the number-average molecular weight, determined by means of GPC, preferably not exceeding about 10,000,000 g/mol, particularly preferably about 5,000,000 g/mol.

In a further preferred embodiment of the process according to the present invention, the content of polymer (A2) in the aqueous composition (A) is adjusted, before the aqueous composition (A) is foamed, to preferably from about 10 to about 90 wt. %, particularly preferably from about 20 to about 70 wt. % and more preferably from about 30 to about 60 wt. %, in each case based on the total weight of the aqueous composition (A). The adjustment is preferably made by diluting the aqueous composition (A) with water.

Crosslinkers (A3) which are preferred according to the present invention are compounds that have at least two functional groups capable of reacting with functional groups of the monomers (α1) or (α2) in a condensation reaction (=condensation crosslinkers), in an addition reaction or in a ring-opening reaction (crosslinker class I), or that have polyvalent metal cations (crosslinker class II). The compounds of crosslinker class I effect crosslinking of the polymers by a condensation reaction of the functional groups, while the compounds of crosslinker class II effect crosslinking by electrostatic interaction of the polyvalent metal cation with the functional groups of the monomers (α1) or (α2).

Examples of compounds of crosslinker class I which may be mentioned include polyols, for example ethylene glycol, polyethylene glycols, such as diethylene glycol, triethylene glycol and tetraethylene glycol, propylene glycol, polypropylene glycols, such as dipropylene glycol, tripropylene glycol or tetrapropylene glycol, 1,3-butanediol, 1,4-butanediol, 1,5-pentanediol, 2,4-pentanediol, 1,6-hexanediol, 2,5-hexanediol, glycerol, polyglycerol, trimethylolpropane, polyoxypropylene, oxyethylene-oxypropylene block copolymers, sorbitan fatty acid esters, polyoxyethylene sorbitan fatty acid esters, pentaerythritol, polyvinyl alcohol and sorbitol, amino alcohols, for example ethanolamine, diethanolamine, triethanolamine or propanolamine, polyamine compounds, for example ethylenediamine, diethylenetriamine, triethylenetetraamine, tetraethylenepentaamine or pentaethylenehexaamine, polyglycidyl ether compounds, such as ethylene glycol diglycidyl ether, polyethylene glycol diglycidyl ether, glycerol diglycidyl ether, glycerol polyglycidyl ether, pentaerythritol polyglycidyl ether, propylene glycol diglycidyl ether, polypropylene glycol diglycidyl ether, neopentyl glycol diglycidyl ether, hexanediol glycidyl ether, trimethylolpropane polyglycidyl ether, sorbitol polyglycidyl ether, phthalic acid diglycidyl ester, adipic acid diglycidyl ether, 1,4-phenylene-bis(2-oxazoline), glycidol, polyisocyanates, preferably diisocyanates, such as 2,4-toluene diisocyanate and hexamethylene diisocyanate, polyaziridine compounds, such as 2,2-bishydroxy-methylbutanol tris[3-(1-aziridinyl) propionate], 1,6-hexamethylenediethyleneurea and diphenylmethane-bis-4,4'-N,N'-diethyleneurea, haloepoxides, for example epichloro- and epibromo-hydrin and α-methylepichlorohydrin, alkylene carbonates, such as 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one, polyquaternary amines, such as condensation products of dimethylamines and epichlorohydrin. As compounds of crosslinker class I, preference is given also to polyoxazolines, such as 1,2-ethylenebisoxazoline, crosslinkers having silane groups, such as γ-glycidoxypropyltrimethoxysilane and γ-aminopropyltrimethoxysilane, oxazolidinones, such as 2-oxazolidinone, bis- and poly-2-oxazolidinones, and diglycol silicates. Ethylene carbonate is particularly preferred as the crosslinker of crosslinker class I.

The polyvalent metal cations of crosslinker class II are preferably derived from mono- or poly-valent cations, the monovalent cations being especially cations of alkali metals, such as potassium, sodium, lithium, with lithium being preferred. Preferred divalent cations are derived from zinc, beryllium, alkaline earth metals, such as magnesium, calcium, strontium, with magnesium being preferred. Further higher-valent cations, which can be used according to the present invention, are cations of aluminium, iron, chromium, manganese, titanium, zirconium and other transition metals, as well as double salts of such cations or mixtures of the mentioned salts. Preference is given to aluminium salts and alums and their various hydrates, such as, for example, $AlCl_3 6H_2O$, $NaAl(SO_4)_2 12\ H_2O$, $KAl(SO_4)_2 12\ H_2O$ or $Al_2(SO_4)_3 14\text{-}18\ H_2O$. Particular preference is given to the use of $Al_2(SO_4)_3$ and its hydrates as crosslinkers of crosslinker class II.

A preferred embodiment of the process according to the present invention is a process in which crosslinkers of the following crosslinker classes or of the following combinations of crosslinker classes are used: I, II, III.

It is further preferred according to the present invention for the crosslinkers (A3) to be used in an amount in a range of from about 0.001 to about 10 wt. %, preferably in a range of from about 0.01 to about 5 wt. % and particularly preferably in a range of from about 1 to about 2.5 wt. %, in each case based on the total weight of the aqueous composition (A).

There are used as blowing agents (A4) in the process according to the present invention preferably compounds that are capable of evolving gas under the process conditions. Preferred blowing agents are, for example, inorganic salts, such as, for example, ammonium carbonate or azo dicarbonate, or organic compounds that are capable of decarboxylation under the process conditions, such as, for example, citric acid.

It is further preferred according to the present invention for the blowing agents (A4) to be used in an amount in a range of from 0.1 to 20 wt. %, preferably in a range of from 1 to 15 wt. % and particularly preferably in a range of from 5 to 12 wt. %, in each case based on the total weight of the aqueous composition (A).

As surfactants (A5) there may be used anionic, cationic, non-ionic or ambivalent surfactants or mixtures thereof. Both low molecular weight and polymeric surfactants can be used. Non-ionic surfactants are, for example, addition products of alkylene oxides, especially ethylene oxide, propylene oxide and/or butylene oxide, with alcohols, amines, phenols, naphthols or carboxylic acids. There are advantageously used as surfactants addition products of ethylene oxide and/or propylene oxide with alcohols containing at least 10 carbon atoms, the addition products containing from about 3 to about 200 mol of ethylene oxide and/or propylene oxide added thereto per mol of alcohol. The addition products contain the alkylene oxide units in the form of blocks or in random distribution. Examples of non-ionic surfactants are the addition products of 7 mol of ethylene oxide with 1 mol of tallow fatty alcohol, reaction products of 9 mol of ethylene oxide with 1 mol of tallow fatty alcohol, and addition products of 80 mol of ethylene oxide with 1 mol of tallow fatty alcohol. Further commercially available non-ionic surfactants consist of reaction products of oxo alcohols or Ziegler alcohols with from 5 to 12 mol of ethylene oxide per mol of alcohol, especially with 7 mol of ethylene oxide. Further commercially available non-ionic surfactants are obtained by ethoxylation of castor oil. From 12 to 80 mol of ethylene oxide, for example, are added per mol of castor oil. Further commercially available products are, for example, the reaction products of 18 mol of ethylene oxide with 1 mol of tallow fatty alcohol, the addition products of 10 mol of ethylene oxide with 1 mol of a $C_{13}/C_{15}$-oxo alcohol, or the reaction products of from 7 to 8 mol of ethylene oxide with 1 mol of a $C_{13}/C_{15}$-oxo alcohol. Further suitable non-ionic surfactants are phenol alkoxylates, such as, for example, p-tert.-butylphenol, which has been, reacted with 9 mol of ethylene oxide, or methyl ethers of reaction products of 1 mol of a $C_{12}$-$C_{18}$ alcohol and 7.5 mol of ethylene oxide.

The above-described surfactants can be converted into the corresponding sulfuric acid semi-esters, for example, by esterification with sulfuric acid. The sulfuric acid semi-esters are used as anionic surfactants in the form of the alkali metal or ammonium salts. Suitable anionic surfactants are, for example, alkali metal or ammonium salts of sulfuric acid semi-esters of addition products of ethylene oxide and/or propylene oxide with fatty alcohols, alkali metal or ammonium salts of alkylbenzenesulfonic acid or alkyl phenol ether sulfates. Products of the mentioned type are available commercially.

Cationic surfactants are also suitable. Examples thereof are the dimethyl-sulfate-quaternised reaction products of 6.5 mol of ethylene oxide with 1 mol of oleylamine, distearyldimethylammonium chloride, lauryltrimethylammonium chloride, cetylpyridinium bromide, and dimethyl-sulfate-quaternised stearic acid triethanolamine esters.

The surfactants (A5) are contained in the aqueous composition (A) preferably in an amount in a range of from about 0.01 to about 15 wt. %, particularly preferably in a range of from about 0.05 to about 10 wt. % and more preferably in a range of from about 0.1 to about 5 wt. %, in each case based on the weight of the aqueous composition (A).

There may be used as auxiliary substances (A6) in the process according to the present invention stabilizers, thickeners, fillers or nucleating agents or mixtures thereof. Thickeners are used, for example, to optimise the structure of the foam and to improve the stability of the foam. Their effect is that the foam shrinks only slightly during the crosslinking of the polymers (A2). There come into consideration as thickeners any natural and synthetic polymers known therefore that greatly increase the viscosity of an aqueous system. Such polymers may be water-swellable or water-soluble synthetic or natural polymers. Superabsorbers in powder form are also suitable as thickeners. A comprehensive overview of thickeners is found, for example, in the publications of R. Y. Lochhead and W. R. Fron, Cosmetics & Toiletries, 108, 95-135 (May 1993) and M. T. Clarke, *"Rheological Additives"* in D. Laba (ed.) *"Rheological Properties of Cosmetics and Toiletries"*, Cosmetic Science and Technology Series, Volume 13, Marcel Dekker Inc., New York 1993.

There are preferably used as fillers chalks, bentonite, talcum, silica gels or silica, activated carbon, pigments, such as titanium dioxide and iron oxide, or mixtures thereof.

The auxiliary substances (A6) are contained in the aqueous composition (A) preferably in an amount in a range of from about 0.01 to about 15 wt. %, particularly preferably in a range of from about 0.05 to about 10 wt. % and more preferably in a range of from about 0.1 to about 5 wt. %, in each case based on the weight of the aqueous composition (A).

In a preferred embodiment of the process according to the present invention, the aqueous composition (A) is obtained by adding the crosslinkers, the blowing agents and optionally the further auxiliary substances to the preferably aqueous polymer solution obtained after polymerization of the monomers ($\alpha$1) and ($\alpha$2) in an aqueous solution.

It is further preferred according to the present invention for the aqueous composition (A) to have a viscosity according to ASTM-D 1824/90 at 20° C. of at least 100 mPa·s, preferably in a range of from about 100 to about 500,000 mPa·s and particularly preferably in a range of from about 500 to about 5,000 mPa·s.

In a preferred embodiment of the process according to the present invention, the composition (A) is so foamed that a foam liter weight in a range of from about 10 to about 1,000 g/l, preferably in a range of from about 50 to about 500 g/l and particularly preferably in a range of from about 80 to about 250 g/l, is obtained.

Foaming of the aqueous composition is preferably carried out by mechanical action, especially by shear, particularly preferably by vigorous stirring or mixing while blending with air. However, it is also possible according to the present invention to foam the composition by the dispersion of an inert gas in the form of fine gas bubbles. The introduction of gas bubbles into the aqueous composition (A) is carried out, for example, with the aid of beating, shaking, stirring or oscillating devices. It is also possible to foam the composition by emitting gases from a liquid-covered opening or by using the phenomenon of turbulence in streams. Furthermore, the provision of platelets on wires or screens can also be used for that purpose. These different methods may optionally also be combined with one another. Suitable inert gases are, for example, nitrogen, carbon dioxide, helium, neon and argon.

Heating of the foamed composition is preferably carried out in an oven, a drying cabinet, using a stream of hot gas, by infrared irradiation or by means of microwave radiation.

In a preferred embodiment of the process according to the present invention, the foamed composition is first transferred to a mould before it is heated. In a further preferred embodiment, the aqueous composition is transferred to a mould before it is foamed and is then foamed in the mould. By subsequently heating the foamed composition in the mould, it is possible to obtain water-absorbent, foam-type polymer structures having a defined spatial structure.

In a further preferred embodiment of the process according to the present invention, the surface of the absorbent, foam-type polymer structure is smoothed, preferably at least partly smoothed, in a further process step. Smoothing of the surface is preferably carried out by wetting the surface with steam at temperatures in a range of from about 20 to about 40° C., followed by calendaring. As a result of the wetting and subsequent calendaring, the pores in the region of the surface of the foam-type polymer structure are preferably compressed slightly, but not closed entirely.

The present invention relates also to a water-absorbent, foam-type polymer structure obtainable by the process described above.

In a preferred embodiment of the water-absorbent, foam-type polymer structure obtainable by the process according to the present invention, said structure has at least one of the following properties:

($\beta$1) an AUL (absorbency under load) of 0.9% NaCl solution under a load of 0.3 psi, (AUL (0.3 psi)), determined according to the test method described herein, of at least about 10 g/g, preferably at least about 13 g/g and particularly preferably at least about 16 g/g;

($\beta$2) a rate of absorption, determined according to the test method described herein, of more than about 1 g/g/sec, preferably more than about 2 g/g/sec and particularly preferably more than about 3 g/g/sec;

($\beta$3) a maximum absorption capacity, determined according to the test method described herein, in a range of from about 20 to about 300 g/g, preferably in a range of from about 30 to about 200 g/g and particularly preferably in a range of from about 35 to about 100 g/g;

($\beta$4) a CRC (centrifugation retention capacity), determined according to the test method described herein, in a range of from about 7.5 to about 100 g/g, preferably in a range of from about 10 to about 80 g/g and particularly preferably in a range of from about 15 to about 60 g/g;

($\beta$5) a mean pore size, determined according to the test method described herein, in a range of from about 0.01 to about 2 mm, preferably in a range of from about 0.1 to about 1 mm and particularly preferably in a range of from about 0.2 to about 0.5 mm;

($\beta$6) a mean weight per unit area, determined according to test method ERT 40.3-90, in a range of from about 60 to about 1200 g/m$^2$, preferably in a range of from about 80 to about 800 g/m$^2$ and particularly preferably in a range of from about 85 to about 500 g/cm$^2$.

Where the foam-type polymer structure is used in hygiene articles for women, especially sanitary towels, a weight per unit area in the range of from about 60 to about 200 g/m$^2$ is preferred, with the range from about 80 to about 100 g/m$^2$ being particularly preferred.

Where the foam-type polymer structure is used in hygiene articles for babies, especially diapers, a weight per unit area in the range of from about 400 to about 1200 g/m$^2$ is preferred, with the range from about 550 to about 800 g/m$^2$ being particularly preferred.

The property combinations of two or more of those properties arising from the above properties each constitute preferred embodiments of the polymer structure according to the present invention. Embodiments according to the present invention which are also particularly preferred are polymer structures which have the properties or combinations of properties shown below as letters or combinations of letters: $\beta$1, $\beta$2, $\beta$3, $\beta$4, $\beta$5, $\beta$6, $\beta$1$\beta$2, $\beta$1$\beta$3, $\beta$1$\beta$4, $\beta$1$\beta$5, $\beta$1$\beta$6, $\beta$2$\beta$3, $\beta$2$\beta$4, $\beta$2$\beta$5, $\beta$2$\beta$6, $\beta$3$\beta$4, $\beta$3$\beta$5, $\beta$3$\beta$6, $\beta$4$\beta$5, $\beta$4$\beta$6, $\beta$5$\beta$6, $\beta$1$\beta$2$\beta$3, $\beta$1$\beta$2$\beta$3$\beta$4, $\beta$1$\beta$2$\beta$3$\beta$4$\beta$5, $\beta$1$\beta$2$\beta$3$\beta$4$\beta$5$\beta$6.

In a preferred embodiment of the water-absorbent, foam-type polymer structures obtainable by the process according to the present invention, said structures have an open-cell structure, a closed-cell structure or a mixed structure of open and closed cells, but preferably an open-cell structure. An open-cell structure is understood to be a structure in which an exchange of liquid is possible between adjacent pores of the foam, while in a closed-cell structure the individual pores are isolated from one another. In a mixed structure of open-cell and closed-cell pores, an exchange of liquid between some adjacent pores is possible by way of common openings in at least two adjacent pores, while other pores are isolated from one another so that no exchange of liquid between those pores by way of common openings in the pores is possible. In a preferred embodiment of the foam-type polymer structure obtainable by the process according to the present invention, at least about 25%, preferably at least about 50% and more preferably at least about 75% of the pores exchange liquid with at least one adjacent pore.

The present invention additionally relates to a water-absorbent, foam-type polymer structure containing (B1) from about 10 to about 99.9 wt. %, preferably from about 20 to about 70 wt. % and particularly preferably from about 30 to about 60 wt. %, in each case based on the total weight of the polymer structure, of one or more crosslinked polymers based at least on (γ1) from about 50 to about 99.99 wt. %, preferably from about 70 to about 99.8 wt. %, of polymerized monoethylenically unsaturated, acid-group-containing monomers or their salts, (γ2) from 0 to about 45 wt. %, preferably from about 0.1 to about 27 wt. %, of polymerized monoethylenically unsaturated monomers that are copolymerizable with (γ1), and (γ3) from about 0.001 to about 5 wt. %, preferably from about 0.1 to about 3 wt. %, of one or more crosslinkers, wherein the sum of the amounts by weight of (γ1) to (γ3) is 100 wt. % and at least about 31.5 wt. % of the monomers, preferably at least about 50 wt. % and particularly preferably at least about 75 wt. %, in each case based on the total weight of the monomers (γ1) and (γ2), are acrylic acid or a salt thereof, (B2) from about 0.01 to about 30 wt. %, preferably from about 0.01 to about 20 wt. % and particularly preferably from about 0.1 to about 10 wt. %, of one or more additives, based on the total weight of the polymer structure, and (B3) from 0 to about 15 wt. %, preferably from about 1 to about 10 wt. % and particularly preferably from about 2 to about 5 wt. %, of water, in each case based on the total weight of the polymer structure and in each case determined by the oven method according to ERT 430.1-99, wherein the sum of the amounts by weight of (B1) to (B3) is 100 wt. % and wherein the water-absorbent, foam-type polymer structure has at least one of the properties (β1) to (β6) mentioned in connection with the water-absorbent, foam-type polymer structure obtainable by the process according to the present invention.

There are present as the additives (B2) preferably the surfactants (A5) and auxiliary substances (A6) mentioned in connection with the process according to the present invention for the preparation of a water-absorbent, foam-type polymer structure.

In a preferred embodiment of the water-absorbent, foam-type polymer structure according to the present invention, said structure has the same properties as already mentioned in connection with the water-absorbent, foam-type polymer structure obtainable by the process according to the present invention.

In a further preferred embodiment of the water-absorbent, foam-type polymer structure according to the present invention, preferred monomers (γ1) and (γ2) and crosslinkers (γ3) are those monomers (α1), (α2) and crosslinkers (A3) which have already been mentioned in connection with the process according to the present invention.

The present invention relates also to a composite comprising the foam-type polymer structure according to the present invention and a substrate. It is preferred for the foam-type polymer structure according to the present invention and the substrate to be firmly bonded to one another. Preferred substrates are films of polymers, such as, for example, of polyethylene, polypropylene or polyamide, metals, nonwovens, fluff, tissues, woven fabrics, natural or synthetic fibers, or other foams.

Because the foamed composition described in connection with the process according to the present invention has a long useful life, it can be applied, for example, to a substrate. The present invention relates also to a process for the production of a composite comprising the water-absorbent, foam-type polymer structure according to the present invention and a substrate, wherein the foamed composition described in connection with the process according to the present invention is brought into contact with at least a portion of the surface of a substrate and the substrate brought into contact with the foamed composition is then heated at a temperature in a range of from about 50 to about 300° C., preferably in a range of from about 100 to about 250° C., so that, preferably whereby, the polymer (A2) crosslinks at least partially, the content of water (A1) is adjusted to not more than about 15 wt. %, preferably to not more than 10 wt. % and particularly preferably to not more than 5 wt. %, in each case based on the total weight of the foam-type polymer structure that forms and in each case determined by the oven method according to ERT 430.1-99, and the resulting foam-type polymer structure is immobilized on at least a portion of the substrate surface (1st process).

In a preferred embodiment of this process according to the present invention, the foamed composition is brought into contact with the surface of the substrate by application of the composition, preferably by spread-coating, knife application or pouring, to the surface of the substrate in a layer having a thickness of from 0.1 to 10 mm, preferably from 1 to 8 mm and particularly preferably from 2 to 4 mm. According to the present invention it is further preferred for the foamed composition to be applied to the substrate in defined areas, for example by the use of templates or screens. In a further preferred embodiment of this process, the foamed composition is applied to layers of fluff and the layers of fluff are accordingly impregnated with the foamed composition, so that the fluff is an integral part of the foam after crosslinking. Preferred substrates in connection with this process are films of polymers, such as, for example, of polyethylene, polypropylene or polyamide, metals, nonwovens, fluff, tissues, woven fabrics, natural or synthetic fibers, or other foams.

A composite containing the water-absorbent, foam-type polymer structure can also be obtained by bringing at least a portion of the surface of the water-absorbent, foam-type polymer structure into contact with at least a portion of the surface of a substrate and then immobilizing the polymer structure on at least a portion of the surface of the substrate (2nd process). The water-absorbent, foam-type polymer structure may thereby be used in the form of polymer structures having a defined spatial structure, as have been described in connection with the process according to the present invention for the preparation of a water-absorbent, foam-type polymer structure. It is, however, also possible to cut or saw polymer structures having a defined spatial structure from larger blocks of the polymer structure.

In a preferred embodiment of this process, immobilisation of the polymer structure on the surface of the substrate is carried out by at least one of the following process steps:

(δ1) pressing together the substrate and the water-absorbent, foam-type polymer structure with a specific pressure of at least about 0.1 N/cm, preferably of at least about 0.5 N/cm and particularly preferably of at least about 1 N/cm, or pressing together the substrate and the foam-type polymer structure with a pressure of at least about 0.1 N/cm$^2$, preferably of at least about 0.5 N/cm$^2$ and particularly preferably of at least about 1 N/cm$^2$;

(δ2) heating the substrate, which has been brought into contact with the foam-type polymer structure, to a temperature in a range of from about 50 to about 300° C., preferably in a range of from about 100 to about 250° C.

Preferred embodiments of this process are processes characterised by the following process steps or combinations of process steps: δ1, δ2, δ1δ2. The conditions for process steps δ1, δ2 are preferably so chosen that the structure of the foam is not destroyed or is able to re-form after the treatment according to the above-described process.

In a preferred embodiment of this process according to the present invention, immobilisation of the water-absorbent, foam-type polymer structure according to the present invention on the surface of the substrate is carried out by calendaring or by ironing the substrate, which has been brought into contact with the polymer structure. A protective layer is preferably placed on the side of the substrate that is not in contact with the polymer structure. Preferred substrates in connection with this process are thermoplastic sheet-form structures, preferably sheet-form structures that are at least partly meltable, such as, for example, polyethylene films.

It is further preferred according to the present invention that, by means of the process according to the present invention for the production of a composite, sandwich-like structures containing at least two layers of the water-absorbent, foam-type polymer structure and at least two substrate layers are obtainable, as follows: in a first process step, a composite consisting of the water-absorbent, foam-type polymer structure (P1) and a substrate (S1) is produced by either the 1st or 2nd process; in a second process step, a layer of the foamed composition is brought into contact with the surface of the substrate (S1) that is opposite the contact surface between the polymer structure (P1) and the substrate (S1) and immobilized, as described in the 1st process, to form a water-absorbent, foam-type polymer structure (P2); and in a third process step, the surface of the water-absorbent, foam-type polymer structure (P2) that is opposite the contact surface between the polymer structure (P2) and the substrate (S1) is brought into contact and immobilized, as described in the 2nd process, on the substrate (S2). These process steps can be repeated as often as desired, according to the number of layers desired.

The present invention relates also to the composites obtained by the process according to the present invention for the production of a composite. Of those composites, preference is given to the composites sandwich-like structures containing fibers, especially fluff, which can be used as a core in hygiene articles.

The present invention relates also to the use of the water-absorbent, foam-type polymer structures according to the present invention or of the composites according to the present invention in chemical products. Such chemical products are preferably fibers, foils, films, cables, sealing materials, liquid-absorbing hygiene articles, coverings for wounds, carriers for plant- and fungus-growth-regulating compositions, additives for building materials, packaging materials and soil additives.

The present invention relates also to chemical products containing the water-absorbent, foam-type polymer structures according to the present invention or the composites according to the present invention. Preferred chemical products are fibers, foils, films, cables, sealing materials, liquid-absorbing hygiene articles, coverings for wounds, carriers for plant- and fungus-growth-regulating compositions, additives for building materials, packaging materials and soil additives.

Of the above-mentioned chemical products, hygiene articles are preferred. These include sanitary towels, babies' diapers, incontinence articles for adults, of which diapers are particularly preferred.

In a particularly preferred embodiment according to the present invention, the composite is a diaper. The components of the diaper that are other than the absorbent, foam-type polymer structure according to the present invention constitute the substrate of the composite. In a preferred embodiment, the diaper contains a core as described above. In that case, the components of the diaper that are other than the core constitute the substrate of the composite. In general, a composite used as a diaper comprises a water-impermeable bottom layer, a water-permeable, preferably hydrophobic, top layer and a layer containing the absorbent, foam-type polymer structure according to the present invention, which is arranged between the bottom layer and the top layer. The layer containing the absorbent, foam-type polymer structure according to the present invention is preferably a core described above. The bottom layer can contain any materials known to the person skilled in the art, with polyethylene or polypropylene being preferred. The upper layer can likewise contain any suitable materials known to the person skilled in the art, with polyester, polyolefins, viscose and the like being preferred, which materials yield a layer of sufficient porosity to ensure adequate penetration of liquid through the top layer. Reference is made in this connection to the disclosure of U.S. Pat. No. 5,061,295, U.S. Pat. No. Re. 26,151, U.S. Pat. No. 3,592,194, U.S. Pat. No. 3,489,148 and U.S. Pat. No. 3,860,003.

The present invention will now be explained in greater detail with reference to non-limiting test methods and examples.

TEST METHODS

Determination of the Foam Liter Weight

To this end, a given amount of composition (A) is foamed to the 1-liter mark in a 1-liter measuring cylinder of known weight.

Determination of the Absorption Under Load (AUL)

In order to determine the absorption under load (AUL), 160 mg of the water-absorbent, foam-type polymer structure, which corresponded to the dimensions of the plastics cylinder, were weighed into a plastics cylinder with wire gauze in the bottom and loaded with a defined weight, which exerts a pressure of 0.3 psi on the polymer structure. The cylinder unit is weighed and placed on a filter plate covered with filter paper and impregnated with 0.9% NaCl solution. The filter plate is submerged in the liquid to its upper edge. Overlapping liquid is to be avoided and the liquid level is to be checked after 20 and 40 minutes. After an absorption time of 1 hour, the cylinder unit is re-weighed and the AUL is determined from the weights. The AUL is defined as the weight of NaCl solution absorbed per gram of the polymer structure.

Determination of the Rate of Absorption

In order to determine the rate of absorption of the water-absorbent, foam-type polymer structure, a circular test area of diameter 40 mm is punched out of the polymer structure and weighed. 5 g of a 0.9% sodium chloride solution stained with methylene blue are weighed into a Petri dish of 60 mm diameter and placed flat on a white substrate. The test area is allowed to fall vertically from a height of 10 mm into the Petri dish filled with the solution. The time from the moment at which the test area comes into contact with the surface of the liquid to the time at which the liquid has been completely absorbed by the test area is stopped. Five determinations are carried out, and the rate of absorption of the structure is indicated in g/g/sec.

Determination of the Maximum Absorption Capacity

The maximum absorption capacity of the water-absorbent, foam-type polymer structure was determined using a 0.9% NaCl solution. A section of polymer structure weighing about 1 g and having a thickness of approximately from 1 to 5 mm is punched out of a water-absorbent, foam-type polymer structure, weighed (W1) and sealed into a tea-bag. The tea-bag is placed in the test solution for 30 minutes and weighed after a drip time of 10 minutes (W2). A tea-bag without water-absorbent polymer, which is likewise placed in the test solution and whose weight after dripping is likewise determined (W3), is used as the blank value. The maximum absorption capacity was indicated in g/g and calculated as follows:

$$CRC\ value = \frac{W_2 - W_1 - W_3}{W_1}$$

Determination of the Centrifugation Retention Capacity (CRC)

In order to determine the retention of the foam-type structure, the tea-bag test was carried out. A 0.9% NaCl solution was used as the test solution. A section of polymer structure weighing about 1 g and having a thickness of approximately from 1 to 5 mm is punched out of a water-absorbent, foam-type polymer structure, weighed (W1) and sealed into a tea-bag. The tea-bag is placed in the test solution for 30 minutes and then centrifuged for 3 minutes in a centrifuge (23 cm diameter, 1400 rpm) and weighed again (W2). A tea-bag without water-absorbent polymer, whose weight after centrifugation is likewise determined (W3), is used as the blank value. The CRC value was indicated in g/g and calculated as follows:

$$CRC\ value = \frac{W_2 - W_1 - W_3}{W_1}$$

Determination of the Mean Pore Size

The mean pore size was determined by determining the diameter of about 100 different pores of a relaxed cut surface of the foam-type polymer structure by means of a magnifying glass and a ruler and forming the mean value from the measured values so obtained. This determination was repeated on 10 cut surfaces. The average value of those mean values corresponds to the mean pore size.

Determination of the Mean Pore Density

The mean pore density was determined by determining the number of pores detectable in a 1 cm×1 cm area of the surface of a foam-type polymer structure using a magnifying glass and a ruler. The number of pores in a total of about 10 areas was determined and the mean value was calculated from the measured values so obtained. This corresponds to the mean pore density of the diameters of about 20 different pores and the mean value was determined from the measured values so obtained. That mean value corresponds to the mean pore size.

EXAMPLES

Example 1

Preparation of a polyacrylic acid solution, 3.5% Na-neutralized, molecular weight approximately 120,000 g/mol.
Weighed Amounts:

| | |
|---|---|
| 225.74 g | acrylic acid |
| 8.79 g | 50% aqueous sodium hydroxide solution |
| 677.00 g | deionised water |
| 0.66 g | mercaptoethanol |
| 1.17 g | 6% aqueous ascorbic acid solution |
| 8.34 g | 35% aqueous hydrogen peroxide solution |
| 6.00 g | 20% aqueous hydroxylamine hydrochloride solution |

Acrylic acid, sodium hydroxide solution and 477.00 g of deionised water are placed in a flat-ground flask. Nitrogen is passed through the solution for one hour, followed by heating to 30° C. Mercaptoethanol, ascorbic acid solution and 1.45 g of hydrogen peroxide solution are added with stirring, following which the temperature of the solution rises to about 85° C. Stirring is carried out for 30 minutes at a bath temperature of 80° C., and 6.00 g of hydroxylamine hydrochloride solution and 6.89 g of hydrogen peroxide solution are then added. The heating bath is switched off and 200.00 g of deionised water are added, yielding an aqueous 25% polymer solution.

Example 2

Preparation of an acrylic acid-hydroxyethyl methacrylate copolymer, 3.5% Na-neutralized, molecular weight approximately 145,000 g/mol.
Weighed Amounts:

| | |
|---|---|
| 217.72 g | acrylic acid |
| 8.03 g | hydroxyethyl methacrylate |
| 8.48 g | 50% aqueous sodium hydroxide solution |
| 677.00 g | deionised water |
| 0.66 g | mercaptoethanol |
| 1.17 g | 6% aqueous ascorbic acid solution |
| 8.34 g | 35% aqueous hydrogen peroxide solution |
| 6.00 g | 20% aqueous hydroxylamine hydrochloride solution |

Acrylic acid, hydroxyethyl methacrylate and sodium hydroxide solution in 477.00 g of deionised water are placed in a flat-ground flask. Nitrogen is passed through the solution for one hour, followed by heating to 30° C. Mercaptoethanol, ascorbic acid solution and 1.45 g of hydrogen peroxide solution are added with stirring, following which the temperature of the solution rises to about 100° C. Stirring is carried out for 2 hours at a bath temperature of 80° C., and 6.00 g of hydroxylamine hydrochloride solution and 6.89 g of hydrogen peroxide solution are then added, and stirring is carried out for a further one hour at a bath temperature of 80° C. The heating bath is switched off and 200.00 g of deionised water are added, yielding an aqueous 25% polymer solution.

Example 3

Preparation of an acrylic acid-butyl acrylate copolymer, 3.5% Na-neutralized, molecular weight approximately 420,000 g/mol.

Weighed Amounts:

| | |
|---|---|
| 213.97 g | acrylic acid |
| 11.77 g | butyl acrylate |
| 8.34 g | 50% aqueous sodium hydroxide solution |
| 677.00 g | deionised water |
| 0.44 g | mercaptoethanol |
| 1.17 g | 6% aqueous ascorbic acid solution |
| 7.15 g | 35% aqueous hydrogen peroxide solution |
| 6.00 g | 20% aqueous hydroxylamine hydrochloride solution |

Acrylic acid and sodium hydroxide solution in 477.00 g of deionised water are placed in a flat-ground flask. Nitrogen is passed through the solution for one hour, followed by heating to 30° C. Mercaptoethanol, ascorbic acid solution and 1.24 g of hydrogen peroxide solution are added with stirring, and at the same time butyl acrylate is added drop wise in the course of three minutes. The temperature of the solution rises rapidly thereby to about 96° C. Stirring is carried out for 2 hours at a bath temperature of 80° C., and 6.00 g of hydroxylamine hydrochloride solution and 5.91 g of hydrogen peroxide solution are then added, and stirring is carried out for a further one hour at a bath temperature of 80° C. The heating bath is switched off and 200.00 g of deionised water are added, yielding an aqueous, highly viscous 25% polymer solution.

Example 4

Preparation according to the present invention of a water-absorbent, foam-type polymer structure

| | |
|---|---|
| 33.35 g | polymer from Example 1 |
| 0.4 g | Stokal SR (Gebruder Langefeld, Krefeld) |
| 0.5 g | potassium stearate |
| 0.5 g | GLUCOPON ® 225 CS UP (Henkel KGaA, Dusseldorf) |
| 12.18 g | 9.71% sodium hydroxide solution |
| 16.71 g | 15.34% potassium hydroxide solution |
| 0.15 g | DENACOL ® Ex 810 (Nagase Kaseikogyo, Japan) |
| 8.22 g | citric acid monohydrate |
| 4.0 g | ethylene carbonate | are combined and broken up for three minutes by means of a Krupp 3 Mix device. The resulting foam is spread out over an area of 0.1 m² and to a height of 0.2 cm and heated for 15 minutes at 220° C. in an air-circulating drying cabinet. The resulting structure has the following characteristic data:

TABLE 1

| Maximum absorption capacity [g/g] | CRC [g/g] | AUL (0.3 psi) [g/g] | Rate of absorption [g/g/sec] |
|---|---|---|---|
| 95.1 | 31.2 | 25.6 | 7.85 |

Example 5

Preparation according to the present invention of a water-absorbent, foam-type polymer structure
Analogously to Example 4, 33.35 g of copolymer are processed to water-absorbent, foam-type polymer structures. The copolymer is prepared analogously to Example 1, whereby in the molar ratio indicated in Table 2, the corresponding proportion of acrylic acid has been replaced by comonomer.

TABLE 2

| Copolymer of the monomer combination (proportion in mol %) | Maximum absorption capacity (g/g) | CRC (g/g) | AUL (0.3 psi) (g/g) | Rate of absorption (g/g/sec) |
|---|---|---|---|---|
| AA/BA (98/2) | 46.2 | 15.2 | 11.3 | 6.9 |
| AA/BA (99.5/0.5) | 64.1 | 17.5 | 13.1 | 6.6 |
| AA/BA/HEMA (99/0.5/0.5) | 45.8 | 15.8 | 11.7 | 5.2 |
| AA/PEG-MAE (98/2) | 43.5 | 14.5 | 12.4 | 7.0 |
| AA/PEG-MAE (96/4) | 25.5 | 8.1 | 9.5 | 4.5 |
| AA/PEG-MAE (99/1) | 55.8 | 16.6 | 11.9 | 7.5 |
| AA/BA/PEG-MAE (96/2/2) | 50.3 | 16.0 | 11.7 | 5.1 |
| AA/BA/PEG-MAE (97/2/1) | 46.2 | 15.1 | 12.5 | 6.3 |
| AA/BA/PEG-MAE (97/1/2) | 49.1 | 15.1 | 12.2 | 7.1 |
| AA/BA/PEG-MAE (98/1/1) | 55.8 | 17.7 | 12.2 | 6.4 |

AA = acrylic acid
BA = butyl acrylate
HEMA = hydroxyethylmethacrylic acid
PEG-MAE = polyethylene glycol monoallyl ether Example 6

Preparation according to the present invention of a water-absorbent, foam-type polymer structure. Analogously to Example 4, 33.35 g of copolymer are processed to water-absorbent, foam-type polymer structures. The copolymer is prepared analogously to Example 2, adjustment having been made according to the molar ratio indicated in Table 3.

TABLE 3

| Copolymer of the monomer combination (proportion in mol %) | Maximum absorption capacity (g/g) | CRC (g/g) | AUL (0.3 psi) (g/g) | Rate of absorption (g/g/sec) |
|---|---|---|---|---|
| AA/BA (98/2) | 50.5 | 15.3 | 12.5 | 2.3 |
| AA/BA (96/4) | 37.9 | 14.3 | 13.2 | 3.1 |
| AA/BA (99/1) | 59.5 | 18.4 | 11.8 | 9.2 |
| AA/BA (99.5/0.5) | 54.4 | 18.8 | 11.8 | 9.5 |
| AA/HEMA (98/2) | 41.2 | 14.6 | 13.0 | 9.1 |
| AA/BA/HEMA (98/1/1) | 43.1 | 13.5 | 13.0 | 7.4 |
| AA/PEG-MAE (98/2) | 44.3 | 13.4 | 12.0 | 6.2 |
| AA/BA/PEG-MAE (96/2/2) | 37.5 | 12.4 | 12.0 | 4.4 |
| AA/BA (97/3) | 39.2 | 16.0 | 14.4 | 1.6 |
| AA/BA/PEG-MAE (96.5/3/0.5) | 49.0 | 17.4 | 12.6 | 4.2 |
| AA/BA/PEG-MAE (96/3/1) | 45.4 | 13.2 | 12.7 | 3.7 |

AA = acrylic acid
BA = butyl acrylate
HEMA = hydroxyethylmethacrylic acid
PEG-MAE = polyethylene glycol monoallyl ether Example 7

Preparation of a water-absorbent, foam-type polymer structure. Two polymers, prepared analogously to Example 2, are mixed in the ratio indicated in Table 4 and processed analogously to Example 4.

TABLE 4

| Copolymer of the monomer combination (proportion in mol %) | Maximum absorption capacity (g/g) | CRC (g/g) | AUL (0.3 psi) (g/g) | Rate of absorption (g/g/sec) |
|---|---|---|---|---|
| 10% AA/PEG-MAE (98/2) 90% AA/BA (98/2) | 49.0 | 18.2 | 15.2 | 2.6 |
| 25% AA/PEG-MAE (98/2) 75% AA/BA (98/2) | 54.0 | 17.7 | 15.0 | 3.8 |
| 50% AA/PEG-MAE (98/2) 50% AA/BA (98/2) | 51.0 | 17.8 | 14.7 | 5.8 |
| 10% AA/PEG-MAE (98/2) 90% AA/BA (96/4) | 43.2 | 16.4 | 14.1 | 3.2 |
| 25% AA/PEG-MAE (98/2) 75% AA/BA (96/4) | 51.9 | 16.7 | 12.3 | 3.4 |
| 50% AA/PEG-MAE (98/2) 50% AA/BA (96/4) | 50.6 | 15.4 | 13.5 | 3.8 |

AA = acrylic acid
BA = butyl acrylate
HEMA = hydroxyethylmethacrylic acid
PEG-MAE = polyethylene glycol monoallyl ether

Example 8

Preparation according to the present invention of a water-absorbent, foam-type polymer structure using alternative crosslinkers. The polymer is prepared analogously to Example 2, with butyl acrylate being added drop wise in the course of 3 minutes once the polymerization has started. The water-absorbent, foam-type polymer structure is prepared analogously to Example 4. DENACOL® Ex 810 is replaced by the crosslinkers indicated in Table 5.

TABLE 5

| Crosslinker | Amount of crosslinker [g/g] | Maximum absorption capacity [g/g] | CRC [g/g] | AUL (0.3 psi) [g/g] |
|---|---|---|---|---|
| Pentaerythritol | 0.15 | 32.8 | 15.8 | 13.3 |
| Glycerol | 0.20 | 34.2 | 15.9 | 13.1 |
| Sorbitol | 0.15 | 41.3 | 16.7 | 14.5 |
| Glycol | 0.15 | 38.3 | 17.1 | 12.9 |
| PEG 600 | 0.30 | 47.6 | 18.4 | 15.6 |
| PEG 300 | 0.30 | 31.0 | 14.8 | 15.4 |
| Mucic acid | 0.15 | 41.8 | 18.22 | 12.5 |
| DENACOL ® Ex 810 | 0.15 | 39.2 | 16.0 | 14.4 |

Example 9

Preparation according to the present invention of a water-absorbent, foam-type polymer structure. Analogously to Example 4, 33.35 g of copolymer (97 mol of acrylic acid:3 mol of butyl acrylate) are processed to a water-absorbent, foam-type polymer structure.

TABLE 6

| Maximum absorption capacity [g/g] | CRC [g/g] | AUL (0.3 psi) [g/g] | Rate of absorption [g/g/sec] |
|---|---|---|---|
| 35.3 | 11.4 | 17.5 | 2.09 |

Example 10

The preparation according to the present invention of a polymer structure from an acrylic acid-butyl acrylate copolymer (97 mol:3 mol) prepared according to Example 3, the amount of mercaptoethanol being reduced to 0.22 g, however. Analogously to Example 4, 33.35 g of copolymer are processed to a water-absorbent, foam-type polymer structure.

TABLE 7

| Maximum absorption capacity [g/g] | CRC [g/g] | AUL (0.3 psi) [g/g] | Rate of absorption [g/g/sec] |
|---|---|---|---|
| 27.5 | 7.7 | 16.4 | 2.04 |

Example 11

The preparation according to the present invention of a polymer structure from an acrylic acid polymer prepared according to Example 1, the amount of mercaptoethanol being reduced to 0.44 g, however. Analogously to Example 4, 33.35 g of copolymer are processed to a water-absorbent, foam-type polymer structure.

TABLE 8

| Maximum absorption capacity [g/g] | CRC [g/g] | AUL (0.3 psi) [g/g] | Rate of absorption [g/g/sec] |
|---|---|---|---|
| 44.0 | 14.3 | 15.4 | 6.94 |

Example 12

The preparation according to the present invention of a polymer structure from an acrylic acid polymer prepared according to Example 1, the amount of mercaptoethanol being reduced to 0.22 g, however. Analogously to Example 4, 33.35 g of copolymer are processed to a water-absorbent, foam-type polymer structure.

TABLE 9

| Maximum absorption capacity [g/g] | CRC [g/g] | AUL (0.3 psi) [g/g] | Rate of absorption [g/g/sec] |
|---|---|---|---|
| 32.1 | 9.6 | 17.3 | 5.66 |

Example 13

Preparation according to the present invention of a water-absorbent, foam-type polymer structure from an acrylic acid-butyl acrylate copolymer (97 mol:3 mol) using alternative crosslinkers. The polymer from Example 3 is used. The structure is prepared analogously to Example 4. DENACOL® Ex810 is replaced by the crosslinkers indicated in the table.

TABLE 10

| Crosslinker | Amount of crosslinker [g/g] | Maximum absorption capacity [g/g] | CRC [g/g] | AUL (0.3 psi) [g/g] |
|---|---|---|---|---|
| Sorbitol | 0.25 | 48.6 | 15.4 | 20.2 |
| PEG 600 | 0.25 | 51.2 | 15.4 | 21.7 |
| Mucic acid | 0.25 | 66.3 | 19.0 | 20.4 |

TABLE 10-continued

| Crosslinker | Amount of crosslinker [g/g] | Maximum absorption capacity [g/g] | CRC [g/g] | AUL (0.3 psi) [g/g] |
|---|---|---|---|---|
| Hydroxyethylcellulose | 0.25 | 54.2 | 15.7 | 20.1 |
| KYMENE ® ULX | 0.17 g | 81.6 | 24.5 | 17.2 |
| KYMENE ® ULX | 0.25 g | 58.2 | 18.8 | 19.3 |

Example 14

Preparation according to the present invention of a water-absorbent, foam-type polymer structure from an acrylic acid polymer prepared according to Example 1, the amount of mercaptoethanol being reduced to 0.44 g, however. The structure is prepared analogously to Example 4. DENACOL® Ex 810 is replaced by the crosslinkers indicated in the table.

TABLE 11

| Crosslinker | Amount of crosslinker [g/g] | Maximum absorption capacity [g/g] | CRC [g/g] | AUL (0.3 psi) [g/g] |
|---|---|---|---|---|
| Sorbitol | 0.25 | 58.5 | 20.9 | 15.0 |
| Mucic acid | 0.25 | 77.3 | 28.6 | 14.1 |
| Mucic acid | 0.42 | 60.3 | 17.0 | 19.2 |
| Pentaerythritol | 0.25 | 67.5 | 20.1 | 15.5 |
| Trimethylolpropane | 0.25 | 64.4 | 20.9 | 16.6 |
| Hydroxyethylcellulose | 0.25 | 68.4 | 22.7 | 14.4 |
| KYMENE ® ULX | 0.17 g | 79.9 | 21.6 | 19.5 |
| KYMENE ® ULX | 0.25 g | 73.8 | 25.1 | 17.1 |

Example 15

Preparation according to the present invention of a water-absorbent, foam-type polymer structure from acrylic acid polymers using different surfactant additives.

| | |
|---|---|
| 33.35 g | polymer from Example 1 |
| 0.4 g | Stokal SR |
| 0.5 g | surfactant, as indicated in the table |
| 33.42 g | 15.34% potassium hydroxide solution |
| 0.15 g | DENACOL ® Ex 810 |
| 8.22 g | citric acid monohydrate |
| 2.0 g | ethylene carbonate | are combined and broken up for three minutes by means of a Krupp 3 Mix device. The resulting foam is spread out over an area of 0.1 m² and to a thickness of 0.2 cm and heated for 15 minutes at 220° C. in an air-circulating drying cabinet.

The resulting polymer structure has the following characteristic data:

TABLE 12

| Surfactant | Maximum absorption capacity [g/g] | CRC [g/g] | AUL (0.3 psi) [g/g] |
|---|---|---|---|
| GLUCOPON ® 225CS UP | 67.9 | 20.9 | 14.9 |
| GLUCOPON ® EC 650 | 67.3 | 21.4 | 14.6 |
| Rewoteric AM 2C NM | 58.1 | 21.9 | 13.6 |
| REWOTERIC ® AM R 40 | 61.9 | 20.0 | 16.1 |
| REWOTERIC ® AM KSF 40 | 73.7 | 20.3 | 16.7 |

TABLE 12-continued

| Surfactant | Maximum absorption capacity [g/g] | CRC [g/g] | AUL (0.3 psi) [g/g] |
|---|---|---|---|
| Elfan NS 242 A | 64.1 | 19.6 | 14.7 |
| Potassium stearate | 80.2 | 23.9 | 14.8 |
| Cocoamidopropylbetain | 68.1 | 19.7 | 14.3 |

Example 16

Preparation according to the present invention of a water-absorbent, foam-type polymer structure from acrylic acid polymer having a water-impermeable back

| | |
|---|---|
| 33.35 g | polymer from Example 1 |
| 0.4 g | Stokal SR |
| 0.5 g | potassium stearate |
| 0.5 g | GLUCOPON ® 225 CS UP (Henkel, Dusseldorf) |
| 12.18 g | 9.71% sodium hydroxide solution |
| 16.71 g | 15.34% potassium hydroxide solution |
| 0.15 g | DENACOL ® Ex 810 |
| 8.22 g | citric acid monohydrate |
| 4.0 g | ethylene carbonate |
| 1.00 | Estekoll HL 50/200 |
| 1.00 | Sarpifan PA 308 A (Stockhausen GmbH & Co. KG, Krefeld) | are combined and broken up for three minutes by means of a Krupp 3 Mix device. The resulting foam is spread out over an area of 0.1 m² and to a height of 0.2 cm and heated for 15 minutes at 220° C. in an air-circulating drying cabinet. The resulting polymer structure is placed on a polyethylene film (PE film) and ironed between silicon-coated paper strips for 10 minutes using an iron until the structure is firmly bonded to the film.

TABLE 13

| | Maximum absorption capacity [g/g] | CRC [g/g] | AUL (0.3 psi) [g/g] |
|---|---|---|---|
| Before calendaring on PE film | 78.1 | 26.7 | 22.6 |
| After calendaring on PE film | 69.0 | 20.0 | 16.1 |

Example 17

100 g of a foam prepared according to Example 4 were sprayed uniformly with a solution of 15 g of water and 1.5 g of ethylene carbonate. When the ethylene carbonate solution had distributed itself uniformly in the foam for a period of one hour, the foam laden with ethylene carbonate was subjected to after-crosslinking for 60 minutes at 180° C. and dried. An after-crosslinked foam having properties according to Table 14 was obtained.

TABLE 14

| Maximum absorption capacity [g/g] | CRC [g/g] | AUL (0.3 psi) [g/g] | Rate of absorption [g/g/sec] |
|---|---|---|---|
| 95.1 | 28.2 | 29.5 | 9.1 |

The invention claimed is:

1. A process for producing water-absorbent, foam-type polymer structures consisting of the steps of:
    i) preparing an aqueous composition (A) wherein the aqueous composition (A) comprises
        (A1) water,
        (A2) one or more polymers based at least on
            (α1) from about 55 to about 100 wt. % of a polymerized, monoethylenically unsaturated, acid-group-containing monomer or its salt thereof, wherein said polymerized, monoethylenically unsaturated, acid-group-containing monomer is neutralized from about 50 to about 90 mol %;
            (α2) from 0 to about 45 wt. % of a polymerized, monoethylenically unsaturated monomer that is copolymerizable with (α1),
        wherein the sum of the amounts by weight of (α1) and (α2) is 100 wt. % and wherein at least about 31.5 wt. % of the monomers, based on the total weight of the monomers (α1) and (α2), are acrylic acid or salts of acrylic acid,
        (A3) one or more crosslinkers,
        (A4) one or more blowing agents,
        (A5) one or more surfactants,
        (A6) and optionally further auxiliary substances,
    ii) foaming the aqueous composition (A) to make a foamed aqueous composition,
    iii) applying ethylene carbonate to the surface of the foamed aqueous composition of step ii),
    iv) heating the foamed aqueous composition including ethylene carbonate of step iii) to a temperature in a range of from about 50 to about 300° C., so that the polymer (A2) crosslinks at least partially and the content of water (A1) is adjusted to not more than about 15 wt. %, based on the total weight of the foam-type polymer structure that forms,
    v) smoothing the surface of the water-absorbent, foam-type polymer structure of step iv) by treating the surface of the water-absorbent, foam-type polymer structure with steam at temperatures in the range of from about 20° C. to 40° C. followed by calendaring wherein the pores in the region of the surface of the foam-type polymer structure are compressed but not closed resulting in the water-absorbent, foam-type polymer structure having nonuniform cell structure.

2. The process according to claim 1, wherein the foamed aqueous composition polymer has a number-average molecular weight of at least about 10,000 g/mol.

3. The process according to claim 1, wherein the foamed composition has a foam liter weight of from about 10 to about 1000 g/l.

4. A water-absorbent, foam-type polymer structure obtainable by a process according to claim 1.

5. A chemical product comprising a water-absorbent, foam-type polymer structure according to claim 4.

6. A composite comprising a water-absorbent, foam-type polymer structure according to claim 4 and a substrate.

7. A chemical product comprising a composite of claim 6.

8. A process for the production of a composite, wherein at least a portion of the surface of the water-absorbent, foam-type polymer structure obtained by the process of claim 1 is brought into contact with at least a portion of the surface of a substrate, and the polymer structure is then immobilized on at least a portion of the surface of the substrate.

9. The process according to claim 8, wherein the substrate is a thermoplastic sheet-form structure.

10. A composite obtainable by a process according to claim 8.

11. The process according to claim 1, wherein the one or more blowing agents is selected from inorganic salts or organic compounds that are capable of decarboxylation.

12. A process for the production of a composite, comprising the steps of
    i) preparing an aqueous composition (A) wherein the aqueous composition (A) comprises
        (A1) water,
        (A2) one or more polymers based at least on
            (α1) from about 55 to about 100 wt. % of a polymerized, monoethylenically unsaturated, acid-group-containing monomer or its salt thereof, wherein said polymerized, monoethylenically unsaturated, acid-group-containing monomer is neutralized from about 50 to about 90 mol %;
            (α2) from 0 to about 45 wt. % of a polymerized, monoethylenically unsaturated monomer that is copolymerizable with (α1),
        wherein the sum of the amounts by weight of (α1) and (α2) is 100 wt. % and wherein at least about 31.5 wt. % of the monomers, based on the total weight of the monomers (α1) and (α2), are acrylic acid or salts of acrylic acid,
        (A3) one or more crosslinkers,
        (A4) one or more blowing agents,
        (A5) one or more surfactants,
        (A6) and optionally further auxiliary substances,
    ii) foaming the aqueous composition (A) to make a foamed aqueous composition,
    iii) applying ethylene carbonate to the surface of the foamed aqueous composition of step ii),
    iv) contacting the foamed aqueous composition including ethylene carbonate of step iii) with at least a portion of the surface of a substrate,
    v) heating the substrate brought into contact with the foamed aqueous composition of step iv) to a temperature in a range of from about 50 to about 300° C. so that the polymer (A2) crosslinks at least partially, the content of water (A1) is adjusted to not more than about 15 wt. %, based on the total weight of the foam-type polymer structure that forms, and the resulting foam-type polymer structure is immobilized on at least a portion of the surface of the substrate, and
    vi) smoothing the surface of the water-absorbent, foam-type polymer structure of step v by treating the surface of the water-absorbent, foam-type polymer structure with steam at temperatures in the range of from about 20° C. to 40° C. followed by calendaring wherein the pores in the region of the surface of the foam-type polymer structure are compressed but not closed resulting in the water-absorbent, foam-type polymer structure having nonuniform cell structure.

13. The process according to claim 12, wherein the substrate is selected from the group consisting of polymeric film, metal, nonwoven, fluff, tissue, woven fabric, natural fiber, synthetic fiber and foam.

14. The process according to claim 12, wherein templates are used during application of the foamed aqueous composition to the substrate.

15. A composite obtainable by a process according to claim 12.

* * * * *